United States Patent [19]

Shibuya et al.

[11] Patent Number: 5,322,693
[45] Date of Patent: Jun. 21, 1994

[54] LACTONEOTREHALOSE, AND ITS PREPARATION AND USES

[75] Inventors: Takashi Shibuya; Hiroto Chaen; Shuzo Sakai, all of Okayama, Japan

[73] Assignee: Kabushiki Kaisha Hayashibara Seibutsu Kagaku Kenkyujo, Okayama, Japan

[21] Appl. No.: 43,018

[22] Filed: Apr. 5, 1993

Related U.S. Application Data

[62] Division of Ser. No. 772,716, Oct. 7, 1991, Pat. No. 5,218,096.

[51] Int. Cl.$^5$ .......................... A61K 7/00; A61K 9/00
[52] U.S. Cl. .......................... 424/439; 424/48; 424/53; 424/400; 424/401; 424/440; 424/464; 424/479; 426/658; 435/74; 435/97; 435/101; 514/25; 514/54; 514/61; 536/4.1
[58] Field of Search .................. 514/25, 54, 61; 536/4.1; 435/74, 97, 101; 424/400, 401, 439; 426/658

[56] References Cited

U.S. PATENT DOCUMENTS

| | | | |
|---|---|---|---|
| 3,819,484 | 6/1974 | Okada et al. | 435/97 |
| 4,384,898 | 5/1983 | Okada et al. | 435/97 |
| 4,782,045 | 11/1988 | Machida et al. | 514/61 |
| 4,895,838 | 1/1990 | McCluer et al. | 514/61 |
| 4,959,468 | 9/1990 | Ravi et al. | 536/4.1 |
| 4,965,354 | 10/1990 | Yanaki et al. | 536/4.1 |
| 5,019,507 | 5/1991 | Hirikoshi | 435/97 |
| 5,032,509 | 9/1991 | Matsamoto et al. | 435/97 |

FOREIGN PATENT DOCUMENTS

| | | |
|---|---|---|
| 0272095 | 12/1986 | European Pat. Off. |
| 48-098093 | 12/1973 | Japan |
| 62-205793 | 9/1987 | Japan |
| 2-195894 | 8/1990 | Japan |

Primary Examiner—Thurman K. Page
Assistant Examiner—Amy Hulina
Attorney, Agent, or Firm—Browdy and Neimark

[57] ABSTRACT

Lactoneotrehalose, a novel saccharide shown by the formula O-$\beta$-D-galactopyranosyl-(1→4)-O-$\beta$-D-glucopyranosyl $\alpha$-D-glucopyranoside, is prepared by allowing a saccharide-transferring enzyme to act on an aqueous solution containing lactose and amylaceous substance. Lactoneotrehalose is a non-reducing oligosaccharide, extremely stable, readily soluble in water, and substantially free of hygroscopicity, as well as having a satisfiable quality and moderate sweetness. These render lactoneotrehalose very useful in the preparations of orally-administrable products, cosmetics and pharmaceuticals.

7 Claims, 3 Drawing Sheets

LACTONEOTREHALOSE, AND ITS PREPARATION AND USES

This is a division of copending parent application Ser. No. 07/772,716, filed Oct. 7, 1991 now U.S. Pat. No. 5,218,096.

BACKGROUND OF THE INVENTION

1. Field of the Invention

The present invention relates to a novel saccharide, and its preparation and uses, more particularly, it relates to lactoneotrehalose shown by the formula O-β-D-galactopyranosyl-(1→4)-O-β-D-glucopyranosyl α-D-glucopyranoside, and its preparation and uses.

2. Description of the Prior Art

Lactose, which is shown by the formula O-β-D-galactopyranosyl-(1→4)-D-glucose, has been known for long as a sweet saccharide present in milk of mammals. Recent increment in the production of milk products such as butter and cheese has been accompanied with a large amount of lactose as by-product. The reducing properties, susceptivity to the browning reaction and low solubility in solvents of lactose have restricted its use of lactose only to the preparations of chocolate, chewing gum and tablet.

Actually, the production of lactose has exceeded the consumption and this resulted in an excessive stock of lactose, as well as having suppressed the production of lactose.

Various attempts have been made to obtain novel saccharides wherein these properties and demerits of lactose are improved.

For example, Bailey et al. reported in *Nature*, Vol. 176, pp.1164–1165 (1955) their finding that O-β-D-galactopyranosyl-(1→4)-O-[α-D-glucopyranosyl-(1→2)]-D-glucopyranose was formed when microorganisms of the species *Batacoccus arabinosaceous* were cultured a medium containing lactose and sucrose; Okada et at. disclosed in Japanese Patent Laid-Open No.98,093/73 a method to prepare reducing oligosaccharides which comprises subjecting lactose and partial starch hydrolysate to the action of saccharide-transferring enzymes to allow a glucosyl residue from partial starch hydrolysate to the galactosyl residue of lactose; and Igarashi et at. disclosed in Japanese Patent Laid-Open No.205,793/87 a method to prepare O-α-D-glucopyranosyl-(1→3)-O-β-D-galactopyranosyl-(1→4)-D-glucose which contains a step of subjecting lactose and partial starch hydrolysate to the action of α-glucosidase from buckwheat or rice.

The saccharides disclosed in the prior art, however, are all reducing-oligosaccharides which are susceptive to the browning reaction and never improve the drawbacks of lactose.

SUMMARY OF THE INVENTION

There has been a great demand for the development of novel saccharides with a satisfiable stability, water-solubility and sweetness, which are obtainable from lactose and capable of overcoming the drawbacks of lactose.

In order to overcome the above drawbacks of lactose, the present inventors studied various saccharides which are obtainable from lactose by utilizing saccharide-transferring reactions.

As a result, the present inventors discovered that lactoneotrehalose, a novel saccharide shown by the formula O-β-D-galactopyranosyl-(1→4)-O-β-D-glucopyranosyl α-D-glucopyranoside, which unlike intact lactose, had non-reducibility, satisfiable stability, water-solubility and desirable sweetness. Thus, the present inventors accomplished the present invention.

BRIEF DESCRIPTION OF THE ACCOMPANYING DRAWINGS

DETAILED DESCRIPTION OF THE INVENTION

Figure 1:
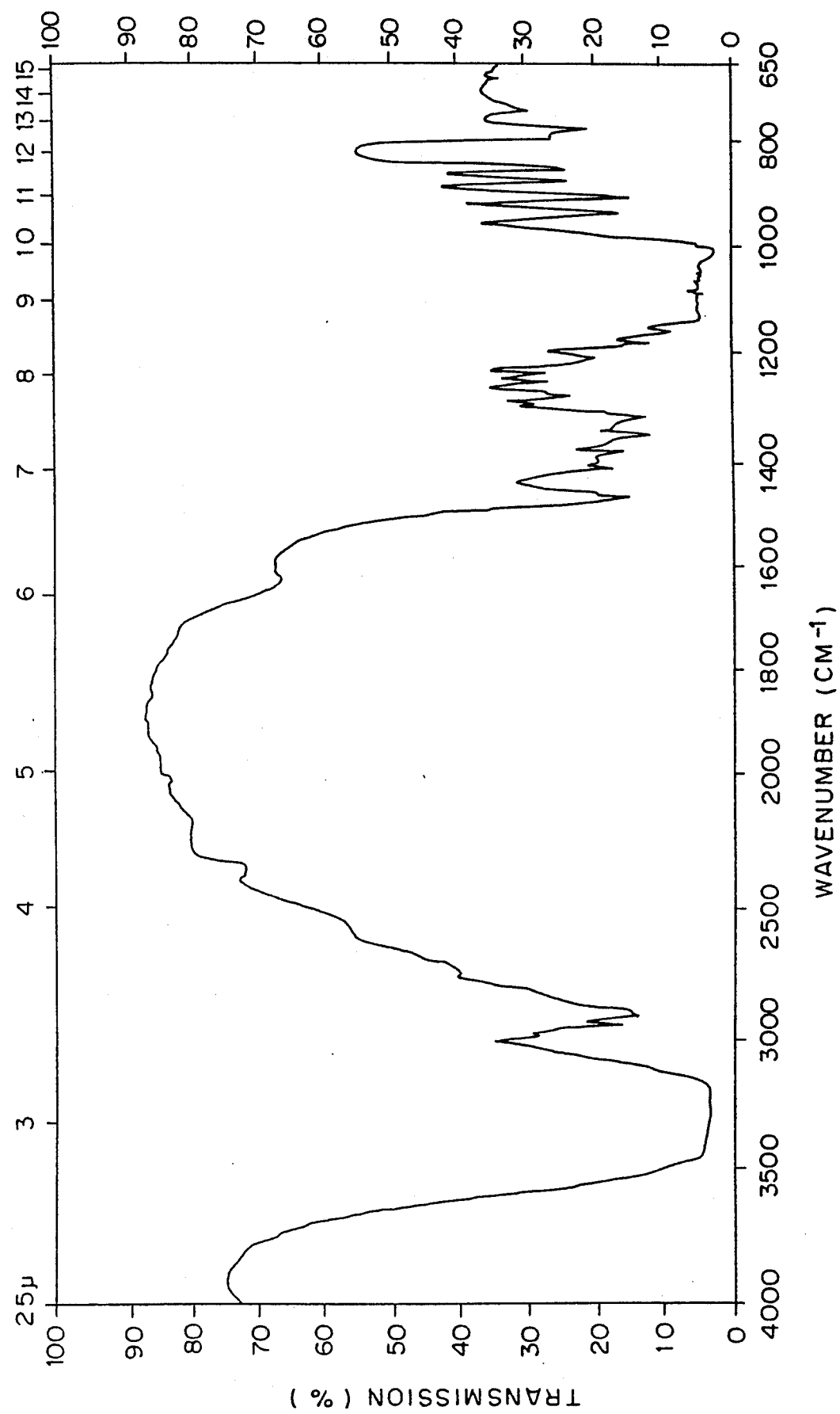
FIG. 1 shows an infrared absorption spectrum of a crystalline lactoneotrehalose specimen.

The present invention relates to lactoneotrehalose shown by the formula O-β-D-galactopyranosyl-(1→4)-O-β-D-glucopyranosyl α-D-glucopyranoside, and its preparation and uses.

Although lactoneotrehalose may be formed through chemical syntheses, much more preferable are biochemical processes wherein lactoneotrehalose is advantageously formed by allowing a saccharide-transferring enzyme to act on an aqueous solution containing lactose and amylaceous substance.

Commercially-available lactoses can be used in the invention. If necessary, crude lactose preparations such as milk and milk serum wherein lactose is present can be used in the invention.

The amylaceous substances advantageously usable in the invention are, for example, gelatinized starch, liquefied starch, solubilized starch, partial starch hydrolysate, and saccharide-transferred amylaceous products.

Although the saccharide-transferring enzyme most preferable in the invention is cyclomaltodextrin glucanotransferase (EC 2.4.1.19), other enzymes such as α-glucosidase (EC 3.2.1.20) and β-galactosidase (EC 3.2.1.23) can be used in the invention.

In the case of using cyclomaltodextrin glucanotransferase, those-derived from microorganisms of the genera Bacillus and Klebsiella can be advantageously used.

The α-glucosidases usable in the invention are, for example, those derived from microorganisms of the genera Penicillium and Mucor. The β-galactosidases usable in the invention are, for example, those derived from microorganisms of the genera Sporoboromyces and Rahnella.

Although any saccharide-transferring reaction can be used in the invention, as long as lactoneotrehalose is formed by the reaction, the reaction conditions are chosen to meet to the enzyme to be used. When cyclomaltodextrin glucano-transferase or α-glucosidase is used as the saccharide-transferring enzyme, either of these is allowed to act on an aqueous solution containing lactose and amylaceous substance such as a partial starch hydrolysate to transfer an α-glucosyl residue from the amylaceous substance to the glucosyl residue of lactose, followed by the formation of lactoneotrehalose. In the above reaction, the preferable weight ratio of amylaceous substance to lactose is usually in the range of 0.1–100 fold, preferably, in the range of 0.2–20 fold. In the case of using β-galactosidase, lactoneotrehalose can be formed by allowing β-galactosidase to act on an aqueous solution containing lactose and neotrehalose, which is an amylaceous saccharide-transferred product, to transfer the β-galactosyl residue from lactose to the glucosyl residue of neotrehalose. In this case, preferable weight ratio of amylaceous substance to lactose is usually in the range of 0.01–10 fold, preferably, in the range of 0.05–2 fold.

In the above reactions, the temperature and pH are usually chosen from 20°–80° C. and 3–9 respectively, while the enzymes can be immobilized for repeated use, if necessary.

Among these saccharide-transferring reactions, the method using cyclomaltodextrin glucanotransferase is generally most favorable because it can attain a higher lactoneotrehalose yield with cheaper amylaceous substances as saccharide donor. In particular, the use of cyclomaltodextrin glucanotransferase derived from *Bacillus stearothermophilus* is extremely favorable from industrial view point because the cyclomaltodextrin glucanotransferase can be allowed to act on substrate at a relatively-high temperature, and this inhibits the retrogradation of amylaceous substance in a reaction solution and the contamination of microorganisms, as well as facilitating the saccharide-transferring reaction.

In this case, one or more units/g amylaceous substance, preferably, 10–1,000 units/g amylaceous substance of cyclomaltodextrin glucanotransferase is allowed to act on an aqueous solution containing lactose together with amylaceous substance such as gelatinized starch, liquefied starch, amylodextrin, cyclodextrin and partial starch hydrolysate having a dextrose equivalent (DE) of about 1–50, for about 1–100 hours, preferably, for about 4–70 hours, to form lactoneotrehalose together with oligosaccharides, for example, α-glycosyl lactoneotrehalose such as α-glucosyl lactoneotrehalose, α-maltosyl lactoneotrehalose, α-maltotriosyl lactoneotrehalose and α-maltotetraosyl lactoneotrehalose, wherein one or more α-glucosyl residues are bound to lactoneotrehalose. These oligosaccharides are then subjected to glucoamylase to form and accumulate lactoneotrehalose, followed by recoverying the accumulated lactoneotrehalose.

Replacement of glucoamylase with β-amylase leads to the formation and accumulation of lactoneotrehalose, α-glucosyl lactoneotrehalose and maltose.

The above saccharide-transferring reactions with or without a hydrolyric reaction form a lactoneotrehalose-containing solution containing usually about 5–40% of lactoneotrehalose, on the dry solid basis (hereinafter abbreviated as "d.s.b."), which is then filtered and purified into liquid, prior to use: Such a liquid may be concentrated, and if necessary, dried into syrup or solid.

In general, in order to augment the merits of lactoneotrehalose, a lactoneotrehalose-containing solution is separated and purified into a high-lactoneotrehalose content product, prior to use. Such separation and purification are achievable, for example, with fermentation using yeast, membrane filtration, fractional-sedimentation, crystalization and/or column chromatography, as long as the concomitant saccharides are removed therewith. In particular, a method wherein column chromatography using strongly-acidic cation exchange resins as disclosed in Japanese Patent Laid-Open Nos.23,799/83 and 72,598/83 can be used to remove concomitant saccharides and to collect lactoneotrehalose-rich fractions. In this case, either of fixed-bed-, moving-bed- and simulated-moving-bed-methods can be suitably employed.

Since lactoneotrehalose is readily crystallizable from the concentrate of the high-lactoneotrehalose content solution, crystalline lactoneotrehalose can be advantageously prepared from the solution, prior to use.

The processes to prepare crystalline lactoneotrehalose according to the present invention usually contain a step of providing a lactoneotrehalose solution with a saturation degree of 1.05–3.5, more particularly, a step of preparing a saccharide composition containing 60% or higher lactoneotrehalose, d.s.b., into a solution having a concentration of about 30–95%; and another step of accelerating the crystallization of lactoneotrehalose by keeping the solution at a temperature which does not freeze the solution and not exceed the melting point of a lactoneotrehalose crystal, for example, in the range of about 10°–100° C.

The crystallization step usable in the invention contains a step of placing in a crystallizer a supersaturated lactoneotrehalose solution which is kept at a relatively-high temperature, i.e. 40°–80° C., and gradually cooling the solution under gentle-stirring conditions, preferably, in the presence of 0.1–20% seed, to accelerate the crystallization. To collect crystalline lactoneotrehalose from the resultant massecuite, any conventional method is employable, as long as crystalline lactoneotrehalose can be obtained thereby; for example, separation-, block-pulverization-, fluidized-bed-granulation and spray-drying-methods. The separation method is to separate a massecuite into crystalline lactoneotrehalose and the mother liquor (molasses) using basket-type centrifuge. If necessary, the resultant crystalline lactoneotrehalose can be readily washed by spraying thereto with a small amount of cool water. Since the other three methods do not remove molasses, they do not improve the purity of lactoneotrehalose in the resultant massecuite, but realize a high-product yield. Accordingly, the product usually contains crystalline lactoneotrehalose together with other saccharide components. The saccharide components vary dependently on the enzymatic reaction used: In the case of using cyclomaltodextrin glucanotransferase in combination with glucoamylase, the final product usually contains lactose and glucose in addition to lactoneotrehalose. In the case of using β-galactosidase, the final product usually contains lactose, neotrehalose and glucose along with lactoneotrehalose.

In the case of the block-pulverization method, a massecuite having a concentration of 85–95% and a crystallinity of about 10–60% is usually allowed to stand for about 0.5–5 days so that the whole content is crystallized and solidified into blocks which are then pulverized by scraping or cutting into a reduced-hygroscopic crystalline powder containing molasses.

In the case of the spray-drying method, a massecuite having a concentration of 65–80% and a crystallinity of about 20–40% is usually spray-dried in the ventilation of a hot air, for example, 60°–100° C. air which does not melt crystalline lactoneotrehalose, and then aged for about 1–20 hours in the ventilation of 30°–60° C. air to obtain a reduced-hygroscopic crystalline lactoneotrehalose powder containing molasses.

The physiological properties of the powders, such as melting point and specific rotation, vary dependently on the lactoneotrehalose content, d.s.b. Usually, the melting point decreases and widens as the lactoneotrehalose content lowers. The hygroscopicity of the powders increases as the lactoneotrehalose content lowers.

Therefore, the lactoneotrehalose content in the powders should be appropriately chosen to meet to their final use.

Lactose is a reducing oligosaccharide which is scarcely soluble in solvents and susceptible to the browning reaction, while unlike lactose, lactoneotrehalose is a non-reducing oligosaccharide which is substantially non-hygroscopic, extremely stable and readily soluble in water, as well as having a high-quality and moderate sweetness. Lactoneotrehalose can be used as a growth-promoting agent for microorganisms of the genus Bifidobacterium because, when orally administered, lactoneotrehalose is mainly assimilated in small intestine as energy source, while a part of the lactoneotrehalose reaches to large intestine to selectively promote the growth of the microorganisms. In addition, since dental-caries-inducing microorganisms scarcely assimilate lactoneotrehalose, it can be used as a sweetener with a reduced dental-caries-inducibility. Since lactoneotrehalose is a sweetener with a satisfiable stability, it can be advantageously used as a sugar-coating agent for tablet in combination with a binder such as pullulan and hydroxyethyl starch. Lactoneotrehalose has a property to stabilize amino acids, oligopeptides and biologically active substances whose effective ingredients and activities may be readily lost, as well as having properties such as a good chemical stability, osmosis-pressure controlling ability, filler-imparting ability, gloss-imparting ability, moisture-retaining ability, decreased fermentability, and crystalization-preventing ability for other saccharides.

These merits would render lactoneotrehalose very useful in the preparations of orally-administrable products, for example, foods, beverages, cigarettes, tobaccos, feeds and pet foods, as well as in the preparations of cosmetics and pharmaceuticals.

Lactoneotrehalose can be used as a seasoning without further treatment to impart sweetness. If necessary, lactoneotrehalose can be used in combination with an adequate amount of one or more other sweeteners, for example, starch sugar powder, glucose, maltose, sucrose, isomerized sugar, honey, maple sugar, sorbitol, dihydrochalcone, stevioside, $\alpha$-glycosyl stevioside, rebaudioside, glycyrrhizin, L-aspartyl L-phenylalanine methyl ester, saccharin, glycine and alanine. Lactoneotrehalose can be mixed with a filler such as dextrin, starch and lactose, prior to use.

Lactoneotrehalose in powder form can be molded solely or after mixing it with filler, vehicle and/or binder into granule, sphere, short-rod, sheet, cubic or tablet, prior to use.

Lactoneotrehalose can be advantageously used in foods and beverages in general to impart to them a sweetness and also to improve their tastes and qualities because lactoneotrehalose has a relatively-high resistance to acid and heat, as well as having a sweetness which well harmonizes with other substances with sour, salty, bitter, delicious and astringent.

Thus, lactoneotrehalose can be advantageously used in foods and beverages in general, for example, seasonings such as soy sauce, say sauce powder, miso, miso powder, "moromi", "hishio", "furikake", mayonnaise, dressing, vinegar, "sanbai-zu", "funmatsu-sushi-su", "chuka-no-moto", "tentsuyu" (soup for tenpura), "mentsuyu" (soup for Japanese-style noodles), Worcester sauce, ketchup, "yakiniku-no-tare" (soup for grilled meat), curry roux, stew premix, soup premix, "dashi-no-moto", mixed seasoning, "mirin" (heavily sweetened sake), "shin-mirin" (synthetic mirin), table sugar and coffee sugar.

Lactoneotrehalose can be advantageously used in foods and beverages in general to impart them a sweetness and to improve their tastes and qualities. Examples of such foods and beverages are Japanese-style confectioneries such as "senbei" (rice crackers), "arare" (pellet-shaped senbei), "okoshi" (millet-and rice cracker), rice paste, "manju" (bun with a bean-jam filling), "uiro" (sweet rice jelly), "an" (bean jam), "yokan" (sweet jelly of beans), "mizu-yokan" (soft adzuki-bean jelly), "kingyoku", jelly, castella and "amedama" (Japanese-style toffee); Western-style confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as those for fruit preserve and "kaki-gori" (shaved ice); pastes such as flour paste, peanut paste, fruit paste and spread; processed fruits such as jam, marmalade, syrup-preserved fruit and crystallized fruit; processed foods of vegetables; pickled products such as "fukujin-zuke" (sliced vegetables picked in soy sauce), "bettara-zuke" (fresh radish pickles), "senmai-zuke" and "rakkyo-zuke"(pickled shallots); premixes for pickled products such as "takuan-zuke-no-moto" and "hakusai-zuke-no-moto"; meat products such as ham and sausage; fish meat products such as fish meat ham, fish meant sausage, "kamaboko" (boiled fish paste), "chikuwa" (literally bamboo wheels) and "tenpura" (deep-fried foods); relishes such as "uni-no-shiokara" (salted guts of sea urchin), "ika-no-shiokara" (salted guts of squid), "sukonbu", "saki-surume" and "fugu-no-mirinboshi"; "tsukudani" (food boiled down in soy sauce) such as those of "nori" (dried seaweed), "sansai" (mountain vegetables), "surume" (dried squid), small fish and shellfish; daily dishes such as "nimame" (cooked beans), potato salad and "konbu-maki" (tangle roll); egg and milk products; bottled and canned products such as those of meat, fish meat, fruit and vegetable; alcoholic drinks such as synthetic sake, "zojo-shu", liqueur, wine and whisky; beverages such as coffee, cocoa, juice, carbonated beverage, lactic acid beverage and lactobacillus beverage; and premixes and instant foodstuffs such as pudding premix, hot cake premix, "sokuseki-shiruko" (premix of adzuki-bean soup with rice cake) and instant soup; and foods and beverages such as baby food, beverage supplemented with nutritional ingredients, and food for medical treatment.

Lactoneotrehalose can be advantageously used in feeds and pet foods for domestic animals and poultries including honey bee, silkworm and pet fish for the improvement of the taste qualities of feeds and pet foods. Lactoneotrehalose can be advantageously used as a sweetener, taste-improving agent and quality-improving agent in special foods and beverages, cosmetics and pharmaceuticals, for example, cigar, cigarette, dentifrice, lipstick, lip cream, internal medicine, troche, cod-liver oil drop, oral refreshing agent, cachou and gargle in the form of a solid, paste or liquid.

In addition, lactoneotrehalose can be advantageously used as a stabilizer, osmosis-pressure controlling agent, filler, humectant, viscosity-controlling agent and quality-improving agent in the preparations of cosmetics such as soap, skin cream, body shampoo, hair cream, lip cream, hair restorer and skin refining agent.

Lactoneotrehalose can be used in biologically active substances to stabilize their effective ingredients and activities: Examples of such biologically active substances are cytokines such as tnterferon, tumor necrosis factor, lymphotoxin, macrophage migration inhibitory factor, colony-stimulating factor, transfer factor and interleukin 2; hormones such as insulin, growth hormone, prolactin, erythropoietin and follicle-stimmulating hormone; vaccines such as BCG vaccine, Japanese encephalitis virus vaccine, measles vaccine, poliomyelitis live vaccine, smallpox vaccine, tetanus toxoid, *Antivenenum Trimeresurus flavoviridis* and human immunoglobulin; antibiotics such as penicillin, erythromycin, chloramphenicol, tetracycline, streptomycin and kanamycin sulfate; vitamins such as thiamine, riboflavin, L-ascorbic acid, cod-liver oil drop, carotenoid, ergosterol and tocopherol; enzymes such as lipase, elastase, urokinase, protease and glucanase; extracts such as ginseng extract, extract of soft-shelled turtle, propolis and royal jelly; and viruses and microorganisms such as a lactobacillus, yeast, and microorganism of the genus *Bifidobacterium*. Lactoneotrehalose can be advantageously used in the preparations of pharmaceuticals as a osmosis-pressure controlling agent, filler, intubation nutrition or sugar for tablet coating.

Any method to incorporate lactoneotrehalose in the products such as orally-administrable products, cosmetics and pharmaceuticals can be used in the invention, as long as lactoneotrehalose is incorporated in the products thereby before completion of their processing. For example, conventional methods such as mixing, kneading, dissolving, melting, soaking, permeating, spreading, applying, coating, spraying, injecting, crystallizing and solidifying are freely chosen. Since crystalline lactoneotrehalose is substantially anhydrous and readily preparable into an absolutely anhydrous crystal, ether- and ester-derivatives of lactoneotrehalose can be advantageously prepared by using a chemical reaction in an anhydrous system, if necessary.

For example, ether- and ester-derivatives of lactoneotrehalose with higher fatty acids can be advantageously used as emulsifier or surfactant.

The lactoneotrehalose according to the present invention will be explained by the following Experiments.

EXPERIMENT

Preparation of Lactoneotrehalose and its Physicochemical Properties

Experiment 1

Preparation of Lactoneotrehalose

Fifty parts by weight of a commercialized lactose and 50 parts by weight of "PINE-DEX #1", a dextrin product (DE 8) commercialized by Matsutani Chemical Ind., Co., Ltd., Hyogo, Japan, were dissolved in 150 parts by weight of water while heating, and the mixture was heated to 60° C., adjusted to pH 6.0, added with 300 units/g dextrin of a cyclomaltodextrin glucanotransferase specimen derived from a microorganism of the species *Bacillus stearothermophilus*, commercialized by Hayashibara Biochemical Laboratories Inc., Okayama, Japan, and allowed to react for 20 hours. Thereafter, the resultant mixture was heated at 100° C. for 30 minutes to inactivate the remaining enzyme, cooled to 55° C., adjusted to pH 5.0, added with 15 units/g dextrin of "Glucozyme", a glucoamylase specimen commercialized by Nagase Biochemicals Ltd., Kyoto, Japan, and allowed to react for 16 hours, followed by heating at 100° C. for 15 minutes to inactivate the remaining enzyme. The resultant solution containing about 24% lactoneotrehalose, d.s.b., which was a novel oligosaccharide according to the present invention, was decolored with an activated charcoal and treated with ion-exchange resins ($H^+$- and $OH^-$-form) for desalting and purification. The resultant solution was concentrated to give a concentration of about 45% and subjected to column chromatography, followed by recoverying lactoneotrehalose-rich fractions. "Amberlite XT-1016 ($Na^+$-form)", a strongly-acidic cation exchange resin commercialized by Japan Organo Co., Ltd., Tokyo, Japan, was used as the resin for fractionation in a manner that the resin was suspended in water, and packed in a jacketted-stainless column having an inner diameter of 5.4 cm. Four columns, a gel-bed depth of 5 m long each, were cascaded to give a total gel-bed depth of about 20 m.

Lactoneotrehalose-rich fractions were obtained by adding to the columns a saccharide solution as a material to give 5 v/v % while keeping the inner temperature of the columns at 55° C., and feeding to the columns 55° C. water at a flow rate of SV 0.3 to effect fractionation. A portion of the pooled lactoneotrehalose-rich fractions having a lactoneotrehalose content of about 67%, d.s.b., which had been obtained by repeating the above fractionation step, was concentrated to give a concentration of 75 w/w %, and allowed to stand overnight at 20° C. to effect crystallization. The resultant crystal as a seed crystal was added to a high-lactoneotrehalose content solution, which had been prepared by concentrating the lactoneotrehalose-rich fractions to give a concentration of 70 w/w %, to effect crystallization under gentle-stirring conditions. The resultant massecuite was separated, and the crystal thus obtained was sprayed with a small amount of water to obtain a high-purity crystalline lactoneotrehalose which was then dissolved in water and treated similarly as above to effect recrystallization. Thus, about 3 parts by weight of a high-purity crystalline lactoneotrehalose having a purity of 99.8% or higher was obtained.

Experiment 2

Physicochemical Properties of Lactoneotrehalose

The physicochemical properties of lactoneotrehalose were studied with a high-purity crystalline lactoneotrehalose specimen prepared by the method in Experiment 1.

(1) Elemental analysis: Found; C=42.8%, H=6.4%, O=50.8%; Calculated; C=42.86%, H=6.39%, O=50.75% (for chemical formula $C_{18}H_{32}O_{16}$)

(2) Molecular weight: 504.4

(3) Melting point: 168.5°–169.0° C.

(4) Specific rotation: $[\alpha]_D^{20} = +82.6°$ (c=2.0, $H_2O$)

(5) uv-Absorption spectrum: Exhibiting no characteristic uv-absorption when tested in water.

(6) Infrared absorption spectrum: Two mg of the crystal and 200 mg of dried KBr were mixed by stirring to obtain about 0.6 mm thick transparent tablet, and the infrared spectrum of the crystal was determined therewith. The result was shown in FIG. 1.

(7) Solubility: 21.7 g of the crystal dissolves in 100 g water at 25° C.

Figure 2:
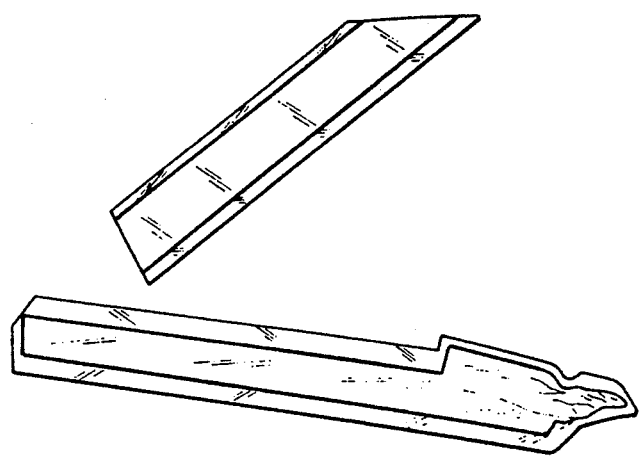
FIG. 2 shows a microscopic photograph (x 50) of a crystalline lactoneotrehalose specimen.

(8) Heat of dissolution: 20.0 cal/g (9) Physical properties and color: Colorless and transparent crystal having a true specific gravity of 1.59. Pulverized crystal has a favorable taste and about ¼ sweetening power of sucrose and exhibits a white appearance, but exhibits no odor. Free of hygroscopicity and deliquescence. The Karl Fischer's method revealed that the moisture content of crystals predried in vacuo at 60° C. for 16 hours is less than 3.0%. FIG. 2 shows a microscopic photograph of a crystal obtained by crystallization in an aqueous solution. An aqueous solution of the crystal shows neutral or slight acidity.

(10) Solubility in solvents: Readily soluble in water, 0.1N sodium hydroxide, and 0.1N hydrochloric acid; scarcely soluble in methanol and ethanol; and insoluble in chloroform and ethyl acetate.

(11) Coloring reaction: Turning green on the anthrone-sulfuric acid reaction. Negative to both the Fehling's reaction and the iodine coloration reaction.

(12) Structure:

(a) Hydrolysis with 1N-sulfuric acid gives 2 moles of D-glucose and one mole of D-galactose.

(b) Gas chromatographic analysis on saccharides obtained by acetylating the crystal with methylhexytol revealed that the crystal formed one mole of 1,5-di-O-acetyl-2,3,4,6-tetra-O-methylglucitol, one mole of 1,5-di-O-acetyl-2,3,4,6-tetra-O-methylgalacitol, and one mole of 1,4,5-tri-O-acetyl-2,3,6-tri-O-methylglucitol.

(c) Infrared absorption spectrum of the crystal gives the absorption near at 910 cm$^{-1}$ inherent to $\beta$-D-galactopyranosyl bond, the absorption near at 880–875 cm$^{-1}$ inherent to $\beta$-D-glucopyranosyl bond, and the absorption near at 860–840 cm$^{-1}$ inherent to $\alpha$-D-glucopyranosyl bond.

(d) When subjected to the action of $\beta$-galactosidase, D-galactose and neotrehalose are formed.

(e) When subjected to the action of $\alpha$-glucosidase, D-glucose and lactose are formed.

(f) On carbon-13 nuclear magnetic resonance ($^{13}$C-NMR) analysis, eighteen $^{13}$C signals were observed and all of eighteen carbons of the crystal showed different chemical shifts respectively. Based on the chemical shifts of $\beta$-D-galactopyranose, $\beta$-D-glucopyranose and $\alpha$-D-glucopyranose as the standard substances reported in J. H. Bradbury et al., *Carbohydrate Research*, Vol.126, pp.125–156 (1984), each carbon of the crystal is assigned to reveal that the crystal has the structure of O-$\beta$-D-galactopyranosyl-(1→4)-O-$\beta$-D-glucopyranosyl $\alpha$-D-glucopyranoside.

Based on the above results, the chemical structure of the crystal can be shown as follows:

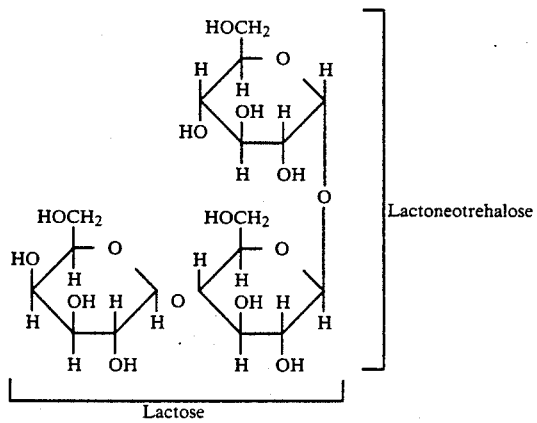

Structure of the Crystal (Lactoneotrehalose)

Based on the above structure, the substance according to the invention is named as lactoneotrehalose.

(13) Powder x-ray diffraction analysis

Figure 3:
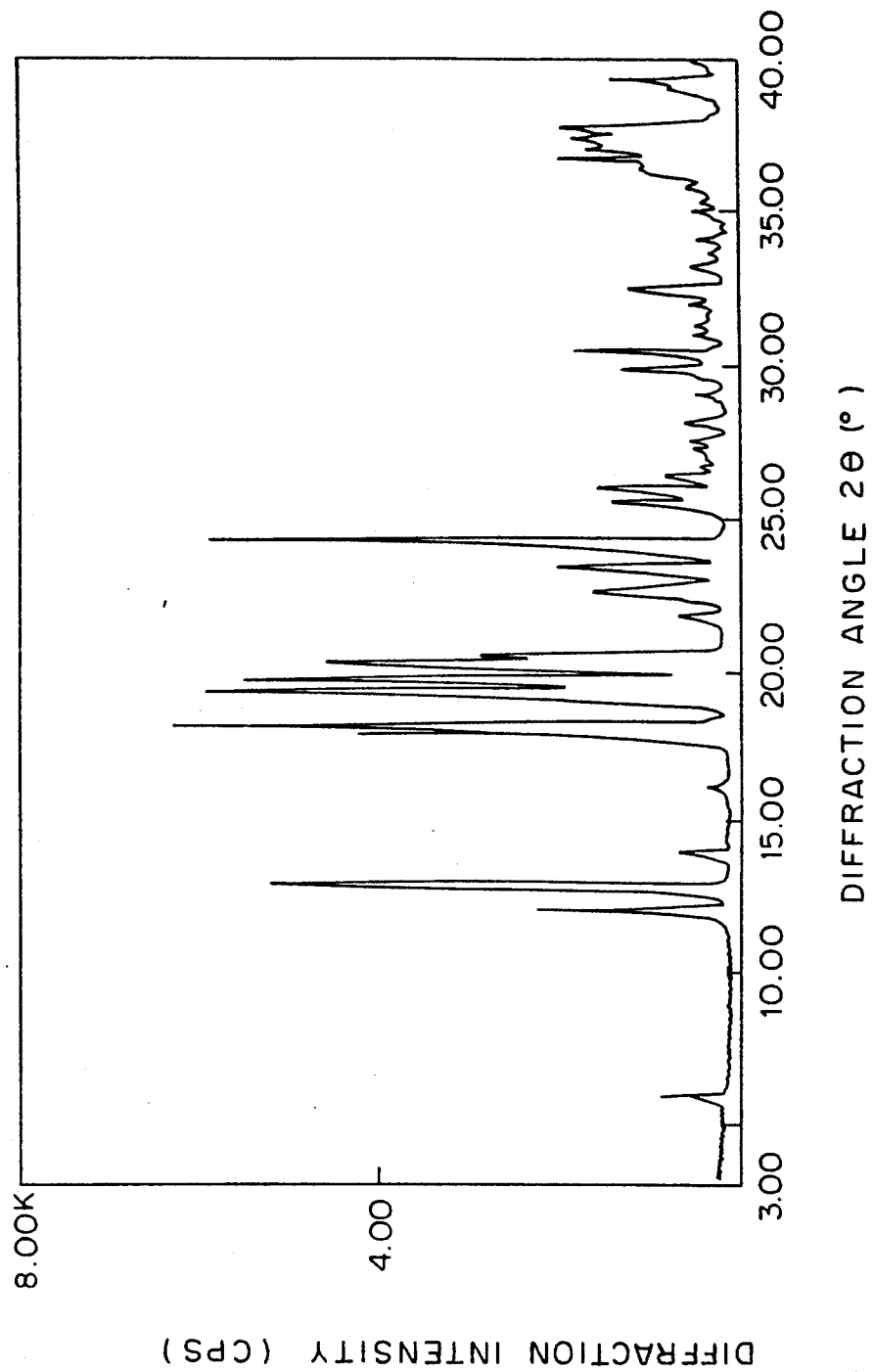
FIG. 3 shows a powder x-ray diffraction pattern of a crystalline lactoneotrehalose specimen.

The powder x-ray diffraction pattern of a crystalline lactoneotrehalose specimen was determined with "GEIGERFLEX RAD-IIB (CuK$\alpha$ ray)", a product of Rigaku Corp., Tokyo, Japan. The results were shown in FIG. 3. As evident from FIG. 3, the crystalline lactoneotrehalose exhibits predominant diffraction angles (2$\theta$) of 12.8°, 18.1°, 19.2°, 19.7° and 24.2° on powder x-ray diffraction analysis.

Experiment 3

Digestion Test

In accordance with the method reported in Okada et al., *Journal of Japanese Society of Nutrition and Food Science*, Vol.43, No.1, pp.23–29 (1990), a crystalline lactoneotrehalose specimen prepared by the method in Experiment 1 was tested for its digestibility in vitro, and the digestibility was evaluated based on the hydrolysis rate (the ratio of reducing sugars against total sugars).

The results were as shown in Table 1.

TABLE 1

| | Hydrolysis rate (%) = $\frac{\text{Reducing sugar}}{\text{Total sugar}} \times 100$ |
|---|---|
| Salivary amylase | 0 |
| Gastric juice | 0 |
| Amylopsin | 0 |
| Enzyme of small intestinal mucous membrane | 60.2 |

As evident from the results in Table 1, it is concluded that lactoneotrehalose is mainly hydrolyzed by the enzyme from intestinal mucous membrane, and the remainder reaches to large intestine.

Experiment 4

Assimilation by Intestinal Microorganism

Intestinal microorganisms were cultured at 37° C. for 96 hours in PYF broth (peptone yeast extract fildes solution broth) reported in Tomotari Mitsuoka, *A Color Atlas of Anaerobic Bacteria*, published by Kabushiki Kaisha Sobunsha, Tokyo, Japan, page 325 (1984), which had been added with or without 0.5 w/v % of a crystalline lactoneotrehalose specimen prepared by the method in Experiment 1. The resultant broth was diluted 5-fold, and the turbidity of the diluted solution was determined at 750 nm in 1-cm cell cuvette. The growth of the intestinal microorganisms and the assimilability of lactoneotrehalose were both evaluated with the turbidity. As control, glucose and lactose were used in place of lactoneotrehalose.

The judgments were as shown in Table 2.

TABLE 2

| Turbidity (A$_{750}$ × 5) | Judgement |
|---|---|
| less than 0.1 | — |
| 0.1 or higher but less than 0.15 | ± |
| 0.15 or higher but less than 0.2 | + |
| 0.2 or higher but less than 0.3 | ++ |
| 0.3 or higher | +++ |

The results were as shown in Table 3.

TABLE 3

| Microorganism | Free of saccharide | Glucose | Lactose | Lactoneotrehalose |
|---|---|---|---|---|
| *Clostridium sporogenes* JCM 1416 | − | ± | − | − |
| *Peptostreptococcus prevotii* ATCC 9321 | − | − | − | − |
| *Streptococcus faecalis* IAM 10065 | − | ++ | + | − |
| *Bifidobacterium adolescentis* JCM 1275 | − | ++ | ++ | ++ |
| *Bifidobacterium animalis* JCM 1190 | − | ++ | ++ | ++ |
| *Bifidobacterium breve* JCM 1192 | − | ++ | +++ | ++ |
| *Bifidobacterium infantis* JCM 1222 | − | ++ | ++ | ++ |
| *Bifidobacterium longum* JCM 1217 | − | ++ | ++ | ++ |
| *Lactobacillus acidophilus* JCM 1132 | − | + | + | ± |
| *Lactobacillus plantarum* IFO 3070 | − | + | + | − |
| *Eubacterium aerofaciens* ATCC 25986 | − | +++ | ++ | − |
| *Eubacterium limosum* JCM 6421 | − | ± | − | − |
| *Bacteroides distasonis* JCM 5825 | − | ± | ± | − |
| *Escherichia coli* IFO 3301 | − | ++ | ± | − |

As evident from the results in Table 3, lactoneotrehalose is a saccharide which is selectively utilized at a relatively high-level by microorganisms of the genus Bifidobacterium.

Combining the results in Experiments 3 and 4, it is concluded that lactoneotrehalose is mainly utilized in small intestine as energy source, and the remainder reaches to large intestine and functions as a growth-promoting agent for microorganisms of the genus Bifidobacterium.

Experiment 5

Acute Toxicity

A crystalline lactoneotrehalose specimen, prepared by the method in Experiment 1, was orally administered to 7 week-old dd mice for acute toxicity test. As a result, no mouse died when administered with up to 5 g of the specimen, and a higher dose test could not done.

These confirmed that the crystalline lactoneotrehalose specimen was extremely low in toxicity.

The following Examples A and Examples B will illustrate the preparations of lactoneotrehalose and its uses respectively.

Example A-1

One part by weight of lactose and 2 parts by weight of "PINE-DEX #4", a dextrin product (DE 18) commercialized by Matsutani Chemical Ind., Co., Ltd., Kyoto, Japan, were dissolved in 3.7 parts by weight of water while heating, and the mixture was heated to 60° C., adjusted to pH 5.6, added with 300 units/g dextrin of a cyclomaltodextrin glucanotransferase specimen commercialized by Hayashibara Biochemical Laboratories, Inc., Okayarea, Japan, and allowed to react for 20 hours. Thereafter, the resultant mixture was heated to inactivate the remaining enzyme, decolored with an activated charcoal, desalted, purified and concentrated into a syrup having a concentration of 75% in the yield of about 92%, d.s.b.

The product containing 15% lactoneotrehalose, d.s.b., exhibits a moderate sweetness, appropriate viscosity and moisture-retaining ability, and these render the product very useful in orally-administrable products, cosmetics and pharmaceuticals.

Example A-2

One part by weight of lactose and 1.5 parts by weight of α-cyclodextrin were dissolved in 4 parts by weight of water while heating, and the mixture first heated to 65° C., adjusted to pH 5.6, added with 200 units/g dextrin of fresh cyclomaltodextrin glucanotransferase as used in Example A-1, and allowed to react for 24 hours. Thereafter, the resultant mixture was first-heated to inactivate the remaining enzyme, then cooled to 55° C., adjusted to pH 5.6, and added with 10 units/g dextrin of "β-amylase #1500", a β-amylase specimen commercialized by Nagase Biochemicals Ltd., Kyoto, Japan, and allowed to react for 16 hours. After completion of the reaction, the mixture was heated to inactivate the remaining enzyme. Similarly as in Example A-1, the resultant mixture was purified and concentrated into a syrup having a concentration of 75% in the yield of about 93%, d.s.b.

The product containing about 25% lactoneotrehalose, d.s.b., exhibits a moderate sweetness, appropriate viscosity and moisture-retaining ability, and these render the product very useful in orally-administrable products, cosmetics and pharmaceuticals similarly as the product in Example A-1.

Example A-3

To a starch slurry having a concentration of 20 w/w % was added 0.15% of "Termamyl 60L", an α-amylase specimen commercialized by Novo Industri A/S, Copenhagen, Denmark, against starch, d.s.b., and the mixture was heated to a temperature in the range of 95°–100° C. to effect liquefaction, and further heated to inactivate the remaining enzyme to obtain a liquefied solution (DE 3) which was then added with lactose equivalent to the amount of amylaceous substance contained in the liquefied solution, d.s.b. The resultant mixture first heated to 55° C., adjusted to pH 5.3, added with 50 units/g starch of an isoamylase specimen commercialized by Hayashibara Biochemical Laboratories Inc., Okayama, Japan, together with 300 units/g starch of the same cyclomaltodextrin glucanotransferase as used in Example A-1, and allowed to react for 24 hours. Thereafter, the mixture thus obtained was heated to inactivate the remaining enzyme, and diluted with water to give a concentration of about 25 w/w %. The resultant was heated to 55° C., adjusted to pH 5.3, added with 15 units/g dextrin of glucoamylase, allowed to react for 16 hours, and heated to inactivate the remaining enzyme. Similarly as in Example A-1, the solution thus obtained was purified and concentrated into a syrup having a concentration of 75% in the yield of about 90%, d.s.b.

The product containing about 34% lactoneotrehalose, d.s.b., exhibits a moderate sweetness, appropriate viscosity and moisture-retaining ability, and these render the product very useful in orally-administrable products, cosmetics and pharmaceuticals similarly as the product in Example A-1.

Example A-4

To a liquefied solution (DE 3) prepared by the method in Example A-3 was dissolved 2-fold amounts of lactose against the amylaceous substance in the liquefied solution, d.s.b. The mixture was heated to 60° C., adjusted to pH 5.6, added with 100 units/g dextrin of cyclomaltodextrin glucanotransferase, allowed to react for 48 hours, and heated to inactivate the remaining enzyme. Similarly as in Example A-3, the resultant mixture was added with glucoamylase to effect an enzymatic reaction and heated to inactivate the remaining enzyme. Similarly as in example A-1, the resultant solution was purified and concentrated into a syrup having a concentration of 75%, which was then transferred to a crystallizer to effect crystallization by the addition of a small amount of lactose. Thereafter, the mixture was centrifuged to remove crystalline lactoneotrehalose and concentrated into a syrup having a concentration of 75% in the yield of about 70%, d.s.b.

The product containing about 35% lactoneotrehalose, d.s.b., exhibits a moderate sweetness, appropriate viscosity and moisture-retaining ability, and these render the product very useful in orally-administrable products, cosmetics and pharmaceuticals similarly as the product in Example A-1.

Example A-5

An about 24% of a high-lactoneotrehalose content solution, d.s.b., prepared by using the reaction- and purification-methods in Experiment 1, as a material saccharide solution, was concentrated to give a concentration of about 45%. In order to higher the lactoneotrehalose content in the resultant solution, which was subjected to column chromatography according to the method in Experiment 1 except that "DOWEX 50Wx4 (Ca++-form)", a strongly-acidic cation exchange resin commercialized by Dow Chemical Company, Midland, Mich., USA, was used as a resin for fractionation to obtain a lactoneotrehalose-rich fraction containing about 70% lactoneotrehalose, d.s.b. The fraction was concentrated to give a concentration of about 83%, and the resultant solution was transferred to a crystallizer and admixed with an about one % seed. The mixture was transferred to a tray and allowed to stand at 20° C. for 4 days to effect crystalization and solidification. Thereafter, the resultant solid was pulverized with a cutting-type pulverizer and dried to obtain a crystalline lactoneotrehalose powder containing molasses in the yield of about 25%, d.s.b.

The product is readily handleable and substantially free of hygroscopicity, and these render the product very useful in orally-administrable products, cosmetics and pharmaceuticals as a sweetener, stabilizer, taste-improving agent and quality-improving agent.

Example A-6

In order to higher the lactoneotrehalose content in an about 35% high-lactoneotrehalose content solution, d.s.b., prepared by using the reaction- and purification-methods in Example A-4, as a material saccharide solution, was subjected to column chromatography according to the method in Example A-5. Thus, a lactoneotrehalose-rich fraction containing about 75% lactoneotrehalose, d.s.b., was obtained. The fraction was concentrated to give a concentration of about 77%, transferred to a crystallizer, added with an about 2% seed, and gradually cooled to obtain a massecuite having a crystallization degree of about 35%, which was then sprayed through a nozzle equipped at the top of a spraying tower with a pressure of 150kg/cm$^2$. Simultaneously, 85° C. air was passed from the top of the tower towards a net conveyer, provided at the bottom of the tower, to collect the pulverized product on the net conveyer and also to gradually carry the resultant crystalline powder out of the tower while passing a stream of 45 ° C. air upwards through the net conveyer. The crystalline powder was then placed in an ageing tower and aged for 10 hours to effect crystallization and dehydration. Thus, a crystalline lactoneotrehalose powder in a crystalline-form containing molasses was obtained in the yield of about 30%, d.s.b.

The product is readily handleable and substantially free of hygroscopicity, and these render the product very useful in orally-administrable products, cosmetics and pharmaceuticals as a sweetener, stabilizer, taste-improving agent and quality-improving agent.

Example A-7

An about 34% high-lactoneotrehalose content solution, d.s.b., prepared by using the reaction- and purification-methods in Example A-3, as a material saccharide solution, was concentrated to give a concentration of about 50%. In order to higher the lactoneotrehalose content in the resultant solution, which was subjected to column chromatography according to the method in Experiment 1 except that "HFS-471X (Na+-form)", a strongly-acidic cation exchange resin commercialized by Japan Organo Co. , Ltd., Tokyo, Japan, was used. Thus, a lactoneotrehalose-rich fraction containing about 80% lactoneotrehalose,-d.s.b., was obtained. The fraction was concentrated to give a concentration of about 75%, transferred to a crystallizer, added with an about one % of a powdery seed, and gradually cooled to effect crystallization under stirring conditions. Thereafter, the resultant was separated by a basket-type centrifuge to obtain a crystal which was then sprayed and washed with a small amount of water to obtain a high-purity crystalline lactoneotrehalose in the yield of about 15%, d.s.b.

Since the product exhibits the same physiological properties as the product in Experiment 2, it can be advantageously used in orally-administrable products, cosmetics and pharmaceuticals as a sweetener, stabilizer, taste-improving agent and quality-improving agent.

Example B-1

Sweetener

One part by weight of a crystalline lactoneotrehalose obtained by the method in Example A-6 was mixed to homogeneity with 0.05 parts by weight of "α-G sweet", an α-glycosyl stevioside product commercialized by Toyo Sugar Refining Co., Ltd., Tokyo, Japan, and the mixture was subjected to a granulator to obtain a sweetener in the form of granule.

Since the sweetener has a satisfiable quality of sweetness and an about 2-fold higher sweetening power of sucrose, the calorific value of the sweetener lowers to about half of that of sucrose per sweetening power.

Since caries-inducing microorganisms less form acids and insoluble glucans when administered the sweetener, the sweetener can be favorably used as a sweetener in caries-preventing foods and beverages.

Example B-2

Hard Candy

One hundred parts by weight of a 55% sucrose solution and 30 parts by weight of a syrup containing lactoneotrehalose, obtained by the method in Example A-2, were mixed by heating. Thereafter, the mixture was concentrated by heating in vacuo until the moisture content decreased to lower than 2%, and further admixed with one part by weight of citric acid and adequate amounts of a coloring agent and lemon flavor. The resultant mixture was formed into the captioned product in an usual manner.

The product is a high-quality hard candy because it has a satisfiable taste and biting property, and because the crystallization of sucrose in the product is prevented.

Example B-3

Strawberry Jam

One hundred and fifty parts by weight of strawberry, 60 parts by weight of sucrose, 20 parts by weight of maltose, 40 parts by weight of a syrup containing lactoneotrehalose obtained by the method in Example A-4, 5 parts by weight of pectin and one part by weight of citric acid were boiled up in a vessel and the mixture was bottled into the captioned product.

The product is a favorable strawberry jam having a satisfiable flavor and color.

Example B-4

Lactic Acid Beverage

Ten parts by weight of defatted milk was sterilized by heating at 80° C. for 20 minutes, cooled to 40° C., added with 0.3 parts by weight of a starter, and fermented at about 37° C. for 10 hours. Thereafter, the mixture was homogenized and added with 4 parts by weight of a crystalline lactoneotrehalose powder obtained by the method in Example A-5, one part by weight of sucrose, and 2 parts by weight of an isomerized syrup. The resultant mixture was sterilized at 70° C., cooled, added with an adequate amount of a flavoring agent, and bottled to obtain the captioned product.

The product is a high-quality lactic acid beverage having a sour taste satisfactorily harmonized with flavor and sweetness.

Example B-5

Sweetened Condensed Milk

To 100 parts by weight of milk was dissolved one part by weight of sucrose and 3 parts by weight of a syrup containing lactoneotrehalose obtained by the method in Example A-1, and the mixture was sterilized by heating with a plate heater, concentrated to give a concentration of about 70%, and aseptically canned to obtain the captioned product.

The product has a moderate sweetness and a satisfiable flavor, and these render the product very useful as seasoning in foods for baby and infant, fruit, coffee, cocoa and tea.

Example B-6

Fruit-Juice Powder

Thirty-three parts by weight of pulverized orange juice prepared by spray-drying was stirred and mixed to homogeneity with 50 parts by weight of a crystalline lactoneotrehalose obtained by the method in Example A-7, 10 parts by weight of sucrose, 0.65 parts by weight of anhydrous citric acid, 0.1 part by weight malic acid, 0.10part by weight of L-ascorbic acid, 0.1 part by weight of sodium citrate, 0.5 parts by weight of pullulan, and an adequate amount of a powdery flavoring agent. The mixture was pulverized, and the resultant powder was fed to a fluidized-bed granulator and granulated at an inlet temperature of 40° C. and an air-flow-rate of 150m³/min for 30 minutes while spraying the content with a high-lactoneotrehalose content solution, obtained by the method in Example A-5, as a binder. Thereafter, the resultant was weighed and packaged to obtain the captioned product.

The product is a fruit-juice powder having an orange juice content of about 30%. The product is free of an unfavorable taste and odor, and stable over a relatively long period of time without being solidified by absorbing moisture.

Example B-7

Chocolate

Forty parts by weight of cacao paste, 10 parts by weight of cacao butter, and 50 parts by weight of a crystalline lactoneotrehalose obtained by the method in Example A-7 were mixed, and the mixture was fed to a refiner to reduce the particle size, transferred to a conche, and kneaded therein at 50° C. for 2 days. In the kneading step, 0.5 parts by weight of lecithin was added and dispersed to homogeneity. Thereafter, the content was adjusted to 31° C. with a thermoregulator, and placed in a mold immediately before the solidification of the butter, deaerated with a vibrator, and solidified by passing it through a 10° C. cooling tunnel over a period of 20 minutes. The content was removed from the mold and packaged to obtain the captioned product.

The product with an excellent color, gloss and texture exhibits no hygroscopicity and smoothly melts in the mouth to exhibit a moderate sweetness and smooth flavor.

Example B-8

Chewing Gum

Three parts by weight of a gum base was melted by heating until it softened, and admixed with 4 parts by weight of sucrose, 3 parts by weight of a crystalline lactoneotrehalose powder obtained by the method in Example A-6, and an adequate amount of a flavoring agent. The mixture was kneaded with a roll in an usual manner, formed and packaged to obtain the captioned product.

The product is a favorable chewing gum having a satisfiable texture and flavor.

Example B-9

Custard Cream

One hundred parts by weight of corn starch, 100 parts by weight of a syrup containing lactoneotrehalose obtained by the method in Example A-4, 80 parts by weight of maltose, 20 parts by weight of sucrose, and one part by weight of salt were mixed to homogeneity. The mixture was admixed with 280 parts by weight of eggs and gradually added with 1,000 parts by weight of a boiling milk. The resultant mixture was heated while stirring, and the heating was stopped when the whole content turned semi-transparent. Thereafter, the resultant product was cooled and added with an adequate amount of vanilla flavor, and the mixture was weighed, filled up and packaged to obtain the captioned product.

The product has a smooth gloss, moderate sweetness and satisfiable taste.

Example B-10

"Uiro-No-Moto" (Premix of Sweet Rice Jelly)

A uiro-no-moto was prepared by mixed to homogeneity with 90 parts by weight of rice powder, 20 parts by weight of corn starch, 120 parts by weight of a crystalline lactoneotrehalose powder obtained by the method in Example A-5, and 4 parts by weight of pullulan. The product was kneaded with adequate amounts of "matcha" (powdered green tea) and water, and the mixture was placed in a vessel and steamed up over a period of 60 minutes to obtain a uiro containing matcha.

The product thus obtained has a satisfiable gloss, biting-property and flavor. The shelf-life of the product is relatively long because the retrogradation of starch in the product is inhibited.

Example B-11

Milky Lotion

One half part by weight of polyoxyethylene behenyl ether, one part by weight of polyoxyethylene sorbitol tetraoleate, one part by weight of oil-soluble glyceryl monostearate, 0.5 parts by weight of behenyl alcohol, one part by weight of avocado oil, 3.5 parts by weight of a syrup containing lactoneotrehalose obtained by the method in Example A-1, one part by weight of $\alpha$-glycosyl rutin, and appropriate amounts of vitamin E and antiseptic were dissolved by heating in an usual manner. The solution was added with 5 parts by weight of 1,3-butylene glycoal, 0.1 part by weight of carboxyvinyl polymer, and 85.3 parts by Weight of refined water. The resultant solution was emulsified by a homogenizer to obtain the captioned product.

The product is a humectant milky-lotion, and this render the product very useful in a sunscreen and skin-whitening agent.

Example B-12

Skin Cream

Two parts by weight of polyoxyethylene glycol monostearate, 5 parts by weight of self-emulsifying glycerine monostearate, 2 parts by weight of $\alpha$-glycosyl rutin, one part by weight of liquid paraffin, 10 parts by weight of glyceryl trioctanate, 4 parts by weight of a crystalline lactoneotrehalose powder obtained by the method in Example A-5, and an appropriate amount of an antiseptic were dissolved by heating in an usual manner, and the mixture was added with 5 parts by weight of 1,3-butylene glycol and 66 parts by weight of refined water. The resultant mixture was emulsified with a homogenizer, added with an appropriate amount of a flavoring agent, and mixed by stirring to obtain the captioned product.

The product is readily spreadable over the skin and favorably usable as a sunscreen, skin-refining agent and skin-whitening agent.

Example-B-13

Dentifrice

A dentifrice was prepared by mixing 13 parts by weight of water with a mixture consisting of 45 parts by weight of calcium secondary phosphate, 1.5 parts by weight of sodium lauryl sulfate, 25 parts by weigh of glycerine, 0.5 parts by weight of polyoxyethylene sorbitan laurate, 15 parts by weight of a syrup containing lactoneotrehalose obtained by the method in Example A-4, 0.02 parts by weight of saccharin, and 0.05 parts by weight of an antiseptic.

The product is a favorable dentifrice having a satisfiable gloss and detergency.

Example B-14

Intubation Nutrition

Twenty four gram aliquots of a composition consisting of 20 parts by weight of a crystalline lactoneotrehalose powder obtained by the method in Example A-6, 1.1 parts by weight of glycine, one part by weight of sodium glutamate, 0.4 parts by weight of calcium lactate, 0.1 part by weight of magnesium carbonate, 0.01 part by weight of thiamine, and 0.01 part by weight of riboflavin were packaged in laminated aluminum bags, and heat-sealed to obtain the captioned product.

In use, one bag of the product is dissolved in about 300-500 ml of water, and the solution is favorably usable as an intubation nutrient directed to parenteral administration into the nasal cavity, gullet and stomach.

The product can be advantageously used as a parenteral intubation-nutrition directed to domestic animals, as well as human.

Example B-15

Intubation Nutrition

Twenty-five gram aliquots of a composition consisting of 580 parts by weight of a crystalline lactoneotrehalose obtained by the method in Example A-7, 190 parts by weight of dried egg, 209 parts by weight of defatted milk, 4.4 parts by weight of salt, 1.85 parts by weight of potassium chloride, 4 parts by weight of magnesium sulfate, 0.01 part by weight of thiamine, 0.1 part by weight of sodium ascorbate, 0.6 parts by weight of vitamin E acetate, and 0.04 parts by weight of nicotinamide were packaged in small laminated-aluminum-bags, and heat-sealed to obtain the captioned product.

In use, one bag of the product is dissolved in about 150-300 ml of water, and the solution is favorably usable as an intubation nutrition directed to parenteral administration into the nasal cavity, stomach and intestine.

Example B-16

Liquid Interferon-Preparation

A natural human interferon-$\gamma$ specimen produced by Hayashibara Biochemical Laboratories Inc., Okayama, Japan, and commercialized by Cosmo Bio Co., Ltd., Tokyo, Japan, was subjected in an usual manner to column chromatography using an immobilized anti-human interferon-$\gamma$ antibody to adsorb thereto the human natural interferon-$\gamma$ contained in the specimen, as well as to remove calf serum-albumin as a stabilizer by passing it through the column. Thereafter, the pH in the column was changed, and the natural human interferon-$\gamma$ was eluted with a physiological saline containing 7% of a crystalline lactoneotrehalose obtained by the method in Experiment 1. The resultant solution was membrane-filtered and aseptically injected into a vial to obtain the captioned product containing $10^5$ units/ml of natural human interferon-$\gamma$.

In use, the product is orally- or parenterally-administered to the adult in an amount of 1-20 ml/day/adult, and can be advantageously used in the treatment of viral diseases, allergic diseases, rheumatism, diabetics, and malignant tumors. Since lactoneotrehalose acts as stabilizer, the activity of natural human interferon-γ is satisfactorily retained even when allowed to stand at 4° C. or 25° C. for 20 days.

Example B-17

Liquid Tumor-Necrosis-Factor Preparation

A natural human tumor necrosis factor specimen produced by Hayashibara Biochemical Laboratories Inc., Okayama, Japan, and commercialized by Cosmo Bio Co., Ltd., Tokyo, Japan, was subjected in an usual manner to column chromatography using an immobilized anti-human tumor necrosis factor-α antibody to adsorb thereto the human natural tumor necrosis factor contained in the specimen, as well as to remove calf serum-albumin as a stabilizer by passing it though the column. Thereafter, the pH in the column was changed, and the natural human tumor necrosis factor-α was eluted from the column with a physiological saline containing 10% of a crystalline lactoneotrehalose obtained by the method in Example A-7. The resultant solution was membrane-filtered and aseptically injected to a vial to obtain the captioned product containing about $10^4$ units/ml of human natural tumor necrosis factor.

In use, the product is orally- or parenterally-administered to the adult in an amount of 1-20 ml/day/adult, and can be advantageously used in the treatment of viral diseases, allergic diseases, rheumatism, diabetics and malignant tumors. Since lactoneotrehalose acts as a stabilizer, the activity of natural human tumor necrosis factor-α is satisfactorily retained even when allowed to stand at 4° C. or 25° C. for 20 days.

Example B-18

Interferon Tablet

A natural human interferon-α specimen produced by Hayashibara Biochemical Laboratories Inc., Okayama, Japan, and commercialized by Cosmo Bio Co., Ltd., Tokyo, Japan, was subjected in an usual manner to column chromatography using an immobilized anti-human interferon-α antibody to adsorb thereto the human natural interferon-α contained in the specimen, as well as to remove calf serum-albumin as a stabilizer by passing it though the column. Thereafter, the pH in the column was changed, and the natural human interferon-α was eluted from the column with a physiological saline containing 5% of a crystalline lactoneotrehalose obtained by the method in Example A-7. The resultant solution was membrane-filtered, and the filtrate was dehydrated and pulverized by the addition of 20-fold volumes of "FINETOSE®", an anhydrous crystalline maltose powder commercialized by Hayashibara Shoji Inc., Okayama, Japan, and the resultant powder was tabletted with a tabletting machine to obtain the captioned product containing about 150 units/tablet of natural human interferon-α, about 200 mg each.

In use, the product is orally-administered to the adult in an amount of 1-10 tablets/day/adult as a sublingual tablet, and can be advantageously used in the treatment of viral diseases, allergic diseases, rheumatism, diabetics and malignant tumors. More particularly, the product can be advantageously used as a therapeutic agent for patients suffering from acquired immune deficiency syndrome (AIDS) and hepatitis, the number of which has been extremely increased recently.

Since lactoneotrehalose and maltose act as a stabilizer, the activity of the product is retained for a relatively long period of time even when allowed to stand at ambient temperature.

Example B-19

Sugar-Coated Tablet

A plain tablet (150 mg in weight) as a core tablet was coated with the first sugar-coating composition consisting of 40 parts by weight of a crystalline lactoneotrehalose obtained by the method in Example A-7, 2 parts by weight of pullulan (average molecular weight of 200,000), 30 parts by weight of water, 25 parts by weight of talc and 3 parts by weight of titanium oxide until the tablet weighed about 230 mg. Thereafter, the resultant tablet was first coated with the second sugar-coating composition consisting of 65 parts by weight of the same crystalline lactoneotrehalose as used in the above, one part by weight of pullulan (average molecular weight of 200,000) and 34 parts by weight of water, then coated with a wax solution to impart a gloss. Thus, the captioned product having a gloss and satisfiable appearance was obtained.

The handleability in the sugar-coating step for the product is satisfactory, and the product has a satisfiable shock-resistance and retains its quality at a relatively high-level over a relatively long period of time. [Effect of the invention]

As described above, the lactoneotrehalose according to the present invention has the following merits: (i) It is a non-reducing oligosaccharide; (ii) It is extremely stable; (iii) It is readily soluble in water, but substantially free of hygroscopicity; and (iv) It has a satisfiable quality and moderate sweetness. Lactoneotrehalose, when orally-administered, is maily utilized in small intestine and used as energy source, and the remainder reaches to large intestine to exert a selective growth-promoting activity for microorganisms of the genus Bifidobacterium.

Lactoneotrehalose has a satisfiable chemical stability and can stabilize amino acids and oligopeptides which are susceptive to the browning reaction, as well as biologically active substances whose effective ingredients and activities may be readily lost. Lactoneotrehalose has merits, for example, osmosis-pressure controlling ability, activating ability, gloss-imparting ability, moisture-retaining ability, viscosity imparting ability, crystallization-preventing ability for other saccharides, and decreased fermentability. These render lactoneotrehalose very useful in the preparations of orally-administrable compositions, cosmetics and pharmaceuticals.

Accordingly, the establishment of lactoneotrehalose, and its preparation and uses have a great, significance in the fields of food-, cosmetic- and pharmaceutical-industries.

While there has been described what is at present considered to be the preferred embodiments of the invention, it will be understood that various modifications may be made therein, and it is intended to cover in the appended claims all such modifications as fall within the true spirit and scope of the invention.

We claim:

1. A pharmaceutical composition, which contains as an effective ingredient lactoneotrehalose shown by the formula O-β-D-galactopyranosyl(1→4)-O-β-D-glucopyranosyl, and by the chemical structure of:

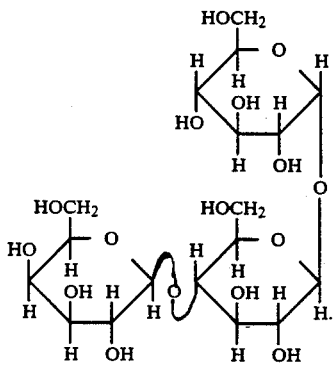

2. The pharmaceutical of claim 1, which additionally contains a biologically active substance.

3. The pharmaceutical of claim 2, wherein said biologically active substance is interferon or tumor necrosis factor.

4. The pharmaceutical of claim 1, which is a growth promoting agent for a microorganism of the genus Bifidobacterium.

5. A cosmetic composition, which contains as an effective ingredient lactoneotrehalose shown by the formula O-β-D-galactopyranosyl(1→4)-O-β-D-glucopyranosyl α-D-glucopyranoside, and by the chemical structure of:

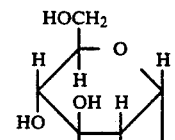

6. An orally-administrable product, a composition that which contains as an effective ingredient lactoneotrehalose shown by the formula O-β-D-galactopyranosyl-)1→4)-O-β-D-glucopyranosyl α-D-glucopyranoside, and by the chemical structure of:

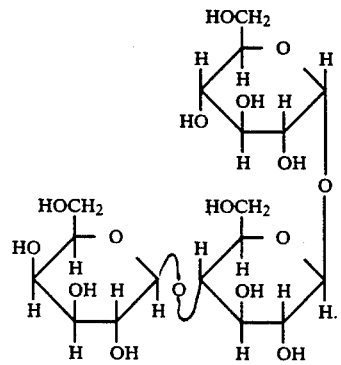

7. The orally-administrable product of claim 6, which is a member selected from the group consisting of foods, beverages, tobaccos, cigarettes, and feeds.

* * * * *